(12) United States Patent
Cornelissen

(10) Patent No.: US 12,130,007 B2
(45) Date of Patent: Oct. 29, 2024

(54) DUAL-REFLECTOR LIGHTING DEVICE

(71) Applicant: SIGNIFY HOLDING B.V., Eindhoven (NL)

(72) Inventor: Hugo Johan Cornelissen, Escharen (NL)

(73) Assignee: SIGNIFY HOLDING B.V., Eindhoven (NL)

( * ) Notice: Subject to any disclaimer, the term of this patent is extended or adjusted under 35 U.S.C. 154(b) by 0 days.

(21) Appl. No.: 18/563,426

(22) PCT Filed: May 20, 2022

(86) PCT No.: PCT/EP2022/063670
§ 371 (c)(1),
(2) Date: Nov. 22, 2023

(87) PCT Pub. No.: WO2022/248343
PCT Pub. Date: Dec. 1, 2022

(65) Prior Publication Data
US 2024/0271774 A1    Aug. 15, 2024

(30) Foreign Application Priority Data
May 27, 2021    (EP) ..................... 21176204

(51) Int. Cl.
*F21V 7/04*     (2006.01)
*A61L 2/10*     (2006.01)
*F21V 7/00*     (2006.01)

(52) U.S. Cl.
CPC ............. *F21V 7/048* (2013.01); *A61L 2/10* (2013.01); *F21V 7/0033* (2013.01); *A61L 2202/11* (2013.01)

(58) Field of Classification Search
CPC ............................ F21V 7/0033; F21V 7/048
(Continued)

(56) References Cited

U.S. PATENT DOCUMENTS

| 2,280,640 A | 4/1942 | Shockey |
| 6,124,600 A | 9/2000 | Moroishi et al. |

(Continued)

FOREIGN PATENT DOCUMENTS

| CN | 106581707 B | 10/2019 |
| DE | 202013000808 U1 | 3/2013 |

(Continued)

*Primary Examiner* — Christopher M Raabe

(57) ABSTRACT

The present invention generally relates to the field of lighting devices, and in particular to a lighting device that is suitable for providing disinfection of an area and/or surrounding environment. The lighting device (100) according to the present invention comprises a light source (101), a first reflector (102), and a second reflector (103). The light source (101) is configured to provide, in operation a light output (111). The first reflector (102) comprising a first reflective surface (121), and the second reflector (103) comprising a second reflective surface (131). The first reflective surface (121) is configured face the second reflective surface (122). The light source (101) is configured to emit the light output (111) towards the second reflective surface (131). The second reflective surface (131) comprises a plurality of sections (133), each section (133) comprising a first section surface (134) that faces away from a center axis (001) of the light source (101) and a second section surface (135) that faces towards the center axis (001). The first section surface (134) comprises a light reflective surface.

15 Claims, 4 Drawing Sheets

(58) Field of Classification Search
USPC .......................................................... 362/297
See application file for complete search history.

(56)             References Cited

U.S. PATENT DOCUMENTS

| | | | |
|---|---|---|---|
| 2009/0004046 A1 | 1/2009 | McEllen | |
| 2009/0049985 A1 | 2/2009 | Leroux et al. | |
| 2014/0084185 A1 | 3/2014 | Palmer et al. | |
| 2016/0091176 A1* | 3/2016 | Wang | F21V 7/28 |
| | | | 362/277 |
| 2017/0130932 A1* | 5/2017 | Longoni | F21V 13/04 |
| 2018/0180226 A1 | 6/2018 | Van Bommel et al. | |
| 2020/0355344 A1 | 11/2020 | Shah et al. | |
| 2023/0054635 A1* | 2/2023 | Kim | G02B 19/0047 |

FOREIGN PATENT DOCUMENTS

| | | |
|---|---|---|
| EP | 2196725 A1 | 6/2010 |
| EP | 2551705 A1 | 1/2013 |
| EP | 3045803 B1 | 4/2018 |
| GB | 2468118 A | 9/2010 |
| JP | 2008204893 A | 9/2008 |
| WO | 2021025063 A1 | 2/2021 |
| WO | 2021043480 A1 | 3/2021 |

\* cited by examiner

DUAL-REFLECTOR LIGHTING DEVICE

CROSS-REFERENCE TO PRIOR APPLICATIONS

This application is the U.S. National Phase application under 35 U.S.C. § 371 of International Application No. PCT/EP2022/063670, filed on May 20, 2022, which claims the benefit of European Patent Application No. 21176204.2, filed on May 27, 2021. These applications are hereby incorporated by reference herein.

FIELD OF THE INVENTION

The present invention generally relates to the field of a lighting device, and in particular to a lighting device that is suitable for providing disinfection of an area and/or surrounding environment.

BACKGROUND OF THE INVENTION

Upper air and surface disinfection systems using germicidal ultraviolet (UV) radiation, usually in the form of UV-C radiation, are known as such. Light in the wavelength range from 100 to 400 nm is called UV light. UV light is relevant for the disinfection of surface, air, and water against microorganisms such as bacteria, viruses, molds, and other pathogens. The germicidal UV radiation disinfects the air and surface by damaging DNA which will inactivate, for example, viruses, bacteria, molds, and yeast that are present in the air. There are three types of UV light classifications based on their wavelength: UV-A (315 to 400 nm), UV-B (280 to 315 nm), and UV-C (100 to 280 nm). The smaller the wavelength of UV light, the higher is the energy of the photons. Highly energetic photons are effective in destroying pathogens. Also, limited exposure to the human skin of UV-B can help produce vitamin D. However, care must be taken when using UV light. Because prolonged exposure to the highly energetic photons of UV light can also severely damage the living tissues of humans and animals. Such disinfection systems are particularly used in places where relatively many people are present for a longer time, for example in office buildings, schools, waiting rooms in hospitals, and in places where there is a high risk for infection by air transmittable diseases such as isolation rooms in hospitals, shelters for homeless people, TBC clinics, etc.

Amongst others, UV-C radiation may be generated by low-pressure mercury (Hg) vapor discharge germicidal lamps, where mercury constitutes the primary component for the generation of UV-C radiation. The discharge vessel of a low-pressure mercury vapor discharge lamp is usually circular and comprises both elongate and compact embodiments. Generally, the tubular discharge vessel of compact fluorescent lamps comprises a collection of relatively short straight parts having a relatively small diameter, while straight parts are connected together by means of bridge parts or via bent parts. The means for maintaining a discharge in the discharge space may be electrodes configured in the discharge space. Alternative to this, a source of UV-C radiation that is currently under investigation is a tile-shaped excimer lamp that emits UV-C light around 222 nm, a wavelength band between 190 nm or more and 230 nm or less. An excimer lamp would be more efficient compared to the low-pressure mercury (Hg) vapor discharge germicidal lamps that emit UV-C light around 254 nm, and also less dangerous for human exposure. The above-mentioned wavelength band is absorbed by the stratum corneum of the skin when applied to the human skin. It does not progress inward (on the basal layer side). Since the stratum corneum contained in the stratum corneum is in a dead state as a cell, it is not absorbed by living cells such as the stratum spinosum, the stratum granulosum, and the dermis, as in the case of being irradiated with ultraviolet rays having a wavelength of 254 nm. There is little risk of DNA destruction.

SUMMARY OF THE INVENTION

A lighting device used as a UV disinfection system may rely on optical elements for realizing desired beam shapes, distributions, and/or patterns for the UV germicidal radiation. For example, to disinfect the surfaces in a tight space from a central lighting device, the radiation must be spread out in a very well-controlled manner, hence requiring customizable beam shaping from such a lighting device. Most cheap materials (e.g. plastic) used for such optical elements in such germicidal systems can be absorptive towards the UV germicidal radiation. This is especially true if the UV germicidal radiation is within the band of UV-C radiation. This may result in comprising the efficiency of the UV germicidal system. Fused silica (quartz) and sapphire can be candidates for refractive optical elements.

It is an object of the present invention to provide a lighting device overcoming, or at least alleviating, one or more of the above-mentioned drawbacks. In particular, it would be desirable to facilitate a lighting device being used as a UV disinfection system that relies on cheap but efficient optical elements for realizing various beam shapes, distributions, and/or patterns for the UV germicidal radiation.

The invention is set out in the appended set of claims. According to a first aspect, this and other objects are achieved by a lighting device according to the present invention comprises a light source, a first reflector, and a second reflector. The light source is configured to provide, in operation a light output. The first reflector comprising a first reflective surface, and the second reflector comprising a second reflective surface. The first reflective surface is configured to face the second reflective surface. The light source is configured to emit the light output in a forward direction along a center axis of the light source towards the second reflective surface. The second reflective surface comprises a plurality of sections, each section comprising a first section surface that faces away from a center axis of the light source and a second section surface that faces towards the center axis. The first section surface comprises a light reflective surface.

In other words, according to a first aspect, this and other objects are achieved by a lighting device according to the present invention comprises a light source, a first reflector, a second reflector, and a light exit window. The light source is configured to provide, in operation a light output. The first reflector comprising a first reflective surface, and the second reflector comprising a second reflective surface. The light exit window is configured between a first edge of the first reflector and a second edge of the second reflector. The first reflective surface is configured to face the second reflective surface. The light source is configured to emit the light output towards the second reflective surface. The second reflective surface comprises a plurality of sections, each section comprising a first section surface that faces away from a center axis of the light source and a second section surface that faces towards the center axis. The first section surface comprises a light reflective surface.

In other words, according to a first aspect, this and other objects are achieved by a lighting device according to the present invention comprises a light source, a first reflector, a second reflector, and a light exit window. The light source is configured to provide, in operation a light output. The first reflector comprising a first reflective surface, and the second reflector comprising a second reflective surface. The light exit window is configured between a first edge of the first reflector and a second edge of the second reflector. The first reflective surface is configured to face the second reflective surface. The first reflective surface encloses a first area and the second reflective surface encloses a second area, the second area being smaller than the first area. The light source is configured to emit the light output in the forward direction along the center axis of the light source towards the second reflective surface. The second reflective surface comprises a plurality of sections, each section comprising a first section surface that faces away from a center axis of the light source and a second section surface that faces towards the center axis. The first section surface comprises a light reflective surface.

In the context of the present invention, the term 'reflector' refers to a device that causes reflection, for example, a mirror or a retroreflector. Therefore, the 'reflector' may comprise a major surface that is light-reflective, herein referred to as a 'reflective surface'. In the context of the present invention, the term 'reflective surface' may be understood but not limited to providing a specular reflection of impinging light. The 'reflective surface' may be configured to provide predominantly specular reflection or a mix of specular and non-specular reflection. The expression "along the center axis" means that the majority of the light output, for example at least 80%, of the light source is within a cone around the center axis, wherein said cone has a half top angle of 45 degrees, e.g. 40 degrees.

The light output from the light source is primarily received by the second reflective surface. Reflective surfaces of the first reflector and the second reflector are configured to face each other. The light source can be located in between the first reflector and the second reflector but configured to emit the light output in the forward direction along the center axis of the light source towards the second reflective surface of the second reflector.

The first reflective surface of the first reflector may have a specular reflection property.

The second reflective surface comprises a plurality of sections. These sections may be regarded as facets that are arranged on the surface of the second reflector. Each section or facet comprises a first section surface that faces away from the center axis of the light source and a second section surface that faces towards the center axis. At least the first section surface comprises a light reflective surface. The light reflective surface of the first section surface may have a specular reflection property. Since the first section surface is configured to face away from the center axis of the light source, at least a part of the light output that is impinging on the first section surface is configured to reflect away from the light source, in a backward direction along the center axis of the light source towards the first reflective surface of the first reflector. If the first reflective surface has specular reflective properties, the light output is further reflected away from the light source again in the forward direction along the center axis of the light source, eventually out of the lighting device if a light exit window is configured between the first reflector and the second reflector. The extent to which the first section surface is facing away from the center axis of the light source may determine the characteristics of the outgoing light from the lighting device, thereby determining the beam shape or pattern of the radiation. Therefore, beam shaping is achieved by employing reflective optical elements in this lighting device.

The first reflector may have a perimeter in the shape of a rectangle, a polygon, or a circle, among others. Similarly, the second reflector may have a perimeter in the shape of a rectangle, a polygon, or a circle, among others.

The light output may have a spectral power distribution in a range of 100 to 400 nm.

The light source may be an ultraviolet light source, potentially can be classified as a UV-A (315 to 400 nm) light source, UV-B (280 to 315 nm) light source, or UV-C (100 to 280 nm) light source.

The light source may be an excimer lamp.

The light output may have a first spectral power distribution that is predominantly distributed around 222 nm.

The light source may be an excimer lamp that is configured to emit in operation that UV-C radiation. Such an excimer lamp may be configured to emit in operation that UV-C radiation having at least spectral power distribution around 222 nm.

The light source may be a UV-C (100 to 280 nm) light source. Potentially, the light source may be an excimer lamp. An excimer lamp having an emission wavelength of 172 nm, which uses Xe gas as a light-emitting gas (discharge gas). Further, various materials other than Xe as a luminescent gas (discharge gas) can be used as an excimer lamp. Specifically, as a combination of luminescent gas and luminescent wavelength, Ar gas is 126 nm, Kr gas is 146 nm, ArBr gas is 165 nm, ArF gas is 193 nm, KrCl gas is 222 nm, XeI gas is 253 nm, and XeBr is 207 nm.

The light source may also be configured to provide, in operation, a light output that is visible light. The color temperature of the light source may be between 2000K and 6500K. In this case, the lighting device may be used to produce various ambient lighting effects.

The light source may comprise multiple emitters that can, in operation, provide visible and UV light. In such a case, the visible light may provide a visual indication of the beam shape, distribution, or pattern of the invisible UV light.

The first reflective surface may be at least partially configured in a first plane that is perpendicular to the center axis, and the light source may have a light emission plane that is substantially parallel to the first plane.

The first reflective surface may be at least partially configured in a first plane, and the light source may have a light emission plane that substantially coincides with the first plane.

The first reflective surface may be at least partially configured in a first plane that is perpendicular to the center axis, and the light source may have a light emission plane that substantially coincides with the first plane.

The first reflective surface may be flat and may be configured in a first plane. The first plane may be perpendicular to the center axis of the light source.

The first reflective surface may a polished metal surface or a mirror surface.

The first reflector may be a flat metal sheet (e.g. aluminum) with a reflective major surface as the first reflective surface.

The first reflector may be flat and also may be configured in a first plane. The first plane may be perpendicular to the center axis of the light source.

The first reflector may have a first reflective surface that is flat and the second reflector may have a second reflective surface comprising a plurality of sections. Other combinations may be also considered. The skilled person may also consider an alternative configuration where, the first reflective surface comprises a plurality of sections instead of being flat, where each section comprises a reflective first section surface that is facing away from a center axis of the light source. While the second reflective surface may comprise a plurality of similar sections, each section comprises a reflective first section surface that is facing away from a center axis of the light source. Or the second reflective surface may be flat as a polished metal surface or mirror surface.

The light source may have a light emission window. The light emission window may be configured in a light emission plane. The light emission plane may coincide with the first plane. Here in the context of the present invention, the term 'coincide' may be understood as overlapping and therefore meaning overlapping of the first plane and the light emission plane. In the context of the present invention, the term 'substantially coincide' may be understood as the planes being close to each other if not overlapping, wherein the separation between the planes may only a few millimeters.

The light emission window may flush with the first reflective surface.

The first reflector may have a through-hole. The perimeter of the through-hole may be at least the same as the light emission window perimeter. Hence, the light output from the light source may transmit through the first reflector. Alternatively, the perimeter of the through-hole may be at least the same as the light source perimeter, hence allowing the light source and/or the light emission window to be placed between the first reflective surface and the second reflective surface.

Alternatively, the light emission window of the light source may be arranged above the first plane of the first reflector having a through-hole. Therefore, the light output from the light source may be transmitted via the through-hole of the first reflector towards the second reflective surface of the second reflector.

The second reflective surface may be configured in a second plane, and each section of the plurality of sections may have a first angle enclosed by the first section surface and the second plane, and the first angle is greater than 10 degrees and less than or equal to 40 degrees.

The second reflective surface may be configured in a second plane that is perpendicular to the center axis, and each section of the plurality of sections may have a first angle enclosed by the first section surface and the second plane, and the first angle is greater than 10 degrees and less than or equal to 40 degrees.

The second reflective surface may be flat and may be configured in a second plane. The first plane may be perpendicular to the center axis of the light source.

The second reflector may be flat and also may be configured in a second plane. The first plane may be perpendicular to the center axis of the light source.

The first angle is an inclination of the first section surface facing away from the center axis. The higher is the first angle, the higher is the reflected angle of the light output from the second reflective surface towards the first reflective surface. A substantially high first angle may cause a loss of light to be reflected from the first light output and/or a loss of reflected light from the first light output if the first reflective surface is not substantially large compared to the second reflective surface. Hence, preferably the first angle may be greater than 10 degrees and less than or equal to 20 degrees.

The first reflector and the second reflector may be configured parallel to each other. Parallel in the context of the invention means out of plane at the most by an angle of five degrees, such as two degrees or zero degrees.

The first reflector and the second reflector may be flat and configured parallel to each other.

The first reflective surface and the second reflective surface may be configured parallel to each other.

The first reflective surface and the second reflective surface may be flat and configured parallel to each other.

At least one of the first reflector and the second reflector may have curved reflective surfaces and yet they can be arranged parallel or non-parallel with respect to each other.

The lighting device may be mounted on a mounting surface (e.g. ceiling) and the first reflective surface and the second reflective surface may be flat and configured parallel to the mounting surface.

The first section surface of each section of the plurality of sections may be flat or curved.

To realize the various beam shapes, distributions, and/or, the first section surface may have a convex or a concave surface. Alternatively, the first section surface may comprise a multi-faceted reflective surface.

Each section of the plurality of sections may be configured adjacent to each other.

The second reflective surface may be at least partially occupied by the plurality of sections.

The second reflective surface may be completely occupied by the plurality of sections.

In the context of the present invention, the term 'adjacent' may be understood as an arrangement of the plurality of sections where there are no gaps or spaces in between the plurality of sections.

The first section surface may have a length that is chosen from a range between 0.2 mm to 5 mm.

The first section surface having a length less than 0.5 mm may be possible when made from materials such as PMMA, PC, or Silicone.

The second reflective surface of the second reflector may be coated with a highly UV-reflective coating, that is potentially a metal (e.g. aluminum coating).

A larger first section surface length of a few millimeters may be made directly from a sheet metal (e.g. aluminum).

The second reflector may be a flat metal sheet (e.g. aluminum) with a reflective surface (e.g. polished) as the second reflective surface that is embossed or diamond-tool machined to realize the plurality of sections.

The second reflective surface may be configured in a second plane that is perpendicular to the center axis, and each section of the plurality of sections may have a second angle enclosed by the second section surface and the second plane, and the second angle may be greater than 50 degrees and less than or equal to 90 degrees.

The second angle may be greater than zero degrees.

The second angle may be the complement of the first angle. In the context of the present invention, the term 'complement' may be understood as a second angle value= (90 degrees—the first angle value).

Preferably, the second angle may greater than 80 degrees and less than or equal to 90 degrees.

The second section surface may comprise a light reflective or light absorptive surface.

The second section surface may be light reflective if the second angle is a complement of the first angle (=90 deg—the first angle) since this may result in some retro-reflection causing recycling and mixing of the light output at the light emission window of the light source. Otherwise, the second section surface can be absorptive for providing more control over the beam shapes, distributions, and/or patterns.

The first reflective surface and the second reflective surface may be separated by a distance that is chosen from a range between 20 to 150 mm.

Depending on the beamwidth of the light output and the first angle of the first section surface, the distance between the first reflective surface and the second reflective surface may be determined.

The distance may be more dependent on the first angle of the first section surface. A higher value (e.g. higher than 10 degrees) of the first angle may result in a shorter distance between the first reflective surface and the second reflective surface, thereby allowing a slim or thin lighting device construction.

The first reflective surface may enclose a first area and the second reflective surface may enclose a second area, and a ratio of the first area and the second area may be chosen from a range between 1.1 to 4.

The first area may be also defined by an area enclosed by the first reflector. Similarly, the second area may be also defined by an area enclosed by the second reflector. The first area may be larger than the second area. A larger first area compared to a second area may help reduce the loss of reflected light from the second reflector towards the first reflector. Preferably, the first area is 2.5 times or less than the second area, since it may not be desired to have a larger reflector that is part of a lighting device.

Each section of the plurality of sections may have the same first angle.

Each section of the plurality of sections may have the same first angle and/or the same second angle.

In this case, each section of the plurality of sections may be identical to each other, which may be easier to produce. The plurality of sections on the second reflective surface may be distributed uniformly.

Each section of the plurality of sections may have different first angles.

Each section of the plurality of sections may have different first angles and/or second angles.

Each section of the plurality of sections may have varying first angles and/or varying second angles with respect to the center axis of the light source along the second plane.

In this case, the plurality of sections on the second reflective surface may be distributed non-uniformly.

A non-uniform distribution of the first angles and/or the second angles will help tune the light distributions (beam shape) and help limit the size of the spot on the first reflector. If the first angle gradually increases from the center axis of the light source towards the second edge of the second reflector, a narrow beam shape of the reflected light will be generated on the first reflective surface, and subsequently, a narrower beam shape for the light output the lighting device is generated when compared to the uniformly distributed plurality of sections. Alternatively, the first angle may be maximum in an area between the center axis of the light source and the second edge of the second reflector, for generating a wider beam shape for the light output from the lighting device when compared to the uniformly distributed plurality of sections.

Each section of the plurality of sections may a length for the first section surface that varies with respect to the center axis of the light source along the second plane.

The varying length of the first section surface may be another example of non-uniform distribution of the plurality of section on the second reflector, which may also be relevant for realizing various beam shapes, distributions, and/or patterns.

Each section of the plurality of sections may a length for the first section surface that is the same with respect to the center axis of the light source along the second plane.

Each section of the plurality of sections may be configured concentrically on the second reflective surface.

The plurality of sections may be considered as facets, similar to a Fresnel lens, except reflective in nature for generating uniform beam shape, distributions, and/or patterns around the center axis of the lighting device.

The sections may be arranged to be concentric on the second reflective surface, rather than discrete sections that as a set or group is facing towards a specific part of the first reflective surface. The plurality of sections may be arranged adjacent to each other, such that there is no gap between the two neighboring sections.

Each section of the plurality of sections may be configured on the second reflective surface such that each of the first section surfaces may be facing away from the center axis of the light source in one or more directions. This direction(s) may be pointing towards areas where it is desired to have the light output from the light source to be illuminated. Therefore, by choosing the appropriate orientation of the first section surfaces, one may realize the high intensity of light in that specific area(s). This may have a beneficial effect on germicidal systems. For the purpose of disinfection, a certain intensity of UV light may determine the dosage required for disinfecting a surface or an area.

According to a second aspect of the present invention, a luminaire is provided that comprises at least one lighting device as described above.

If the light source in the lighting device is configured to provide, in operation a light output having UV spectral component (UV-A, UV-B, UV-C), the luminaire may be used for germicidal or disinfection system that provides disinfection of the air and/or surface.

The second reflector may be replaceable.

In such a case, the luminaire having a provision for replacing the second reflector with other various forms (e.g. various sizes and/or shapes) of the plurality of sections may yield various beam shapes, distribution, and/or patterns that are suitable for various use cases. The use cases, for example, can be only upper air disinfection, disinfection of a narrow space or wide space, etc. For example, the second reflector may be chosen such that a higher dose to some areas is provided, such as the control panel in the elevator.

Alternatively, the first reflector and/or the second reflector may replaceable for producing a wide variety of beam shapes, distribution, and/or patterns.

The luminaire may comprise a presence sensor for disabling the radiation of the UV light from the lighting device if human and/or pet presence is detected in the vicinity of the luminaire.

It is noted that the invention relates to all possible combinations of features recited in the claims. Other objectives, features, and advantages of the present inventive concept will appear from the following detailed disclosure, from the attached claims as well as from the drawings. A feature described in relation to one of the aspects may also be incorporated in the other aspect, and the advantage of the feature is applicable to all aspects in which it is incorporated.

BRIEF DESCRIPTION OF THE DRAWINGS

The above, as well as additional objects, features, and advantages of the disclosed devices, methods, and systems, will be better understood through the following illustrative and non-limiting detailed description of embodiments of devices, methods, and systems, with reference to the appended drawings, in which.

As illustrated in the figures, the sizes of layers and regions are exaggerated for illustrative purposes and, thus, are provided to illustrate the general structures of embodiments of the present invention. Like reference numerals refer to like elements throughout.

DETAILED DESCRIPTION

The present invention will now be described more fully hereinafter with reference to the accompanying drawings, in which currently preferred embodiments of the invention are shown. This invention may, however, be embodied in many different forms and should not be construed as limited to the embodiments set forth herein; rather, these embodiments are provided for thoroughness and completeness, and fully convey the scope of the invention to the skilled person.

Figure 1:
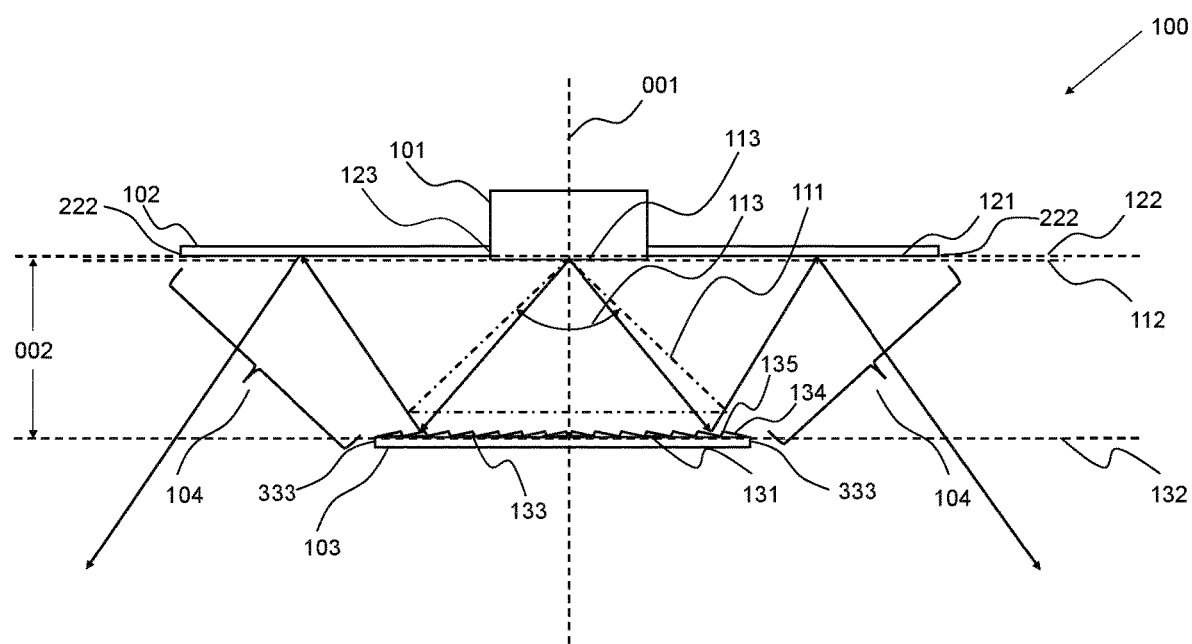
FIG. 1 shows a cross-sectional view of a lighting device.

Referring initially to FIG. 1, a cross-sectional view of a lighting device 100 is shown. The lighting device 100 comprises a light source 101. The light source 101, in operation, is configured to provide a light output 111. The light output 111 has a beamwidth 113, which can be understood as a full-width half-maximum of the light output 111. The light output 111 may have a spectral power distribution in a range of 100 to 400 nm. Therefore, the light source 101 may be a UV source, more specifically, a UV source that can emit UV-A, UV-B, and/or UV-C light. The light source 101 in FIG. 1 is depicted to have a tile shape, which may be suitable for UV-C emitting excimer lamps.

The lighting device 100 further comprises a first reflector 102 and a second reflector 103. The first reflector 102 has a first reflective surface 121, which is a major surface among one other. The first reflective surface 121 is configured in a first plane 122. Therefore, the first reflective surface 121 is flat. The first reflector 102 is depicted to have two first edges 222, therefore the first reflector 102 may have a perimeter in the shape of a rectangle, a polygon, or a circle, among others.

Similar to the first reflector 103, the second reflector 103 is depicted to be flat having a second reflective surface 131 that coincides with a second plane 132. The first reflective surface 121 and the second reflective surface 131 are configured to face each other. And the light source 101 is configured to emit the light output 111 towards the second reflective surface 131. The second reflector 103 is depicted to have two second edges 333, therefore the second reflector 103 may have a perimeter in the shape of a rectangle, a polygon, or a circle, among others.

The light source 101 is configured to be passed via a through-hole 123 of the first reflector 102. The light source 101 has light emission window 113 configured in a light emission plane 112. The light emission plane 112 is parallel and close to the first plane 122. The light emission plane 112 may be located between the first plane 122 and the second plane 132. The light emission plane 112 may also coincide with the first plane 122 such that the light emission window 113 flushes with the first reflective surface 121. Alternatively, the light source 101 may be configured such that the light emission plane 112 may be located out of the first plane 122 and the second plane 132, being closer to the first plane 122 than the second plane 132. The first reflector 102 may not have any through-hole 123 as depicted in FIG. 1, but the light source 101 may be located between the first reflector 102 and the second reflector 103.

In FIG. 1, the light source 101 has a center axis 001 is configured perpendicular to the first plane 122, the light emission plane 112, and the second plane 132. The light source 101, the first reflector 102, and the second reflector 103 are configured symmetrically with respect to the center axis.

In FIG. 1, the first reflector 102 and the second reflector 103 are depicted to be flat and configured parallel to each other. The first reflector 102 and the second reflector 103 may be configured parallel to each other, yet having curved shapes or surfaces. Also, the first reflector 102 and the second reflector 103 may not be configured parallel to each other.

The lighting device 100 comprises a light exit window 104 that is configured between a first edge 222 of the first reflector 102 and a second edge 333 of the second reflector 103. The light output 111 may come out of the light exit window 104 by a first reflection from the second reflector 103 and/or a second reflection from the first reflector 102.

The first reflector 102 and the second reflector 103 are configured to be separated by a distance 002. The distance 002 may be chosen between 20 to 150 mm.

A first area enclosed by the first reflective surface 121 (in this case, the same as the first reflector 102) is larger than a second area that is enclosed by the second reflective surface 131 (in this case, the same as the second reflector 103). A ratio of the first area and the second area may be chosen from a range between 1.1 to 4.

The second reflective surface 131 comprises a plurality of sections 133. Each section 133 comprising a first section surface 134 that faces away from a center axis 001 of the light source 101 and a second section surface 135 that faces towards the center axis 001. The first section surface 134 comprises a light reflective surface. The second section surface 135 may comprise a light reflective surface or a light absorptive surface.

Figure 2:
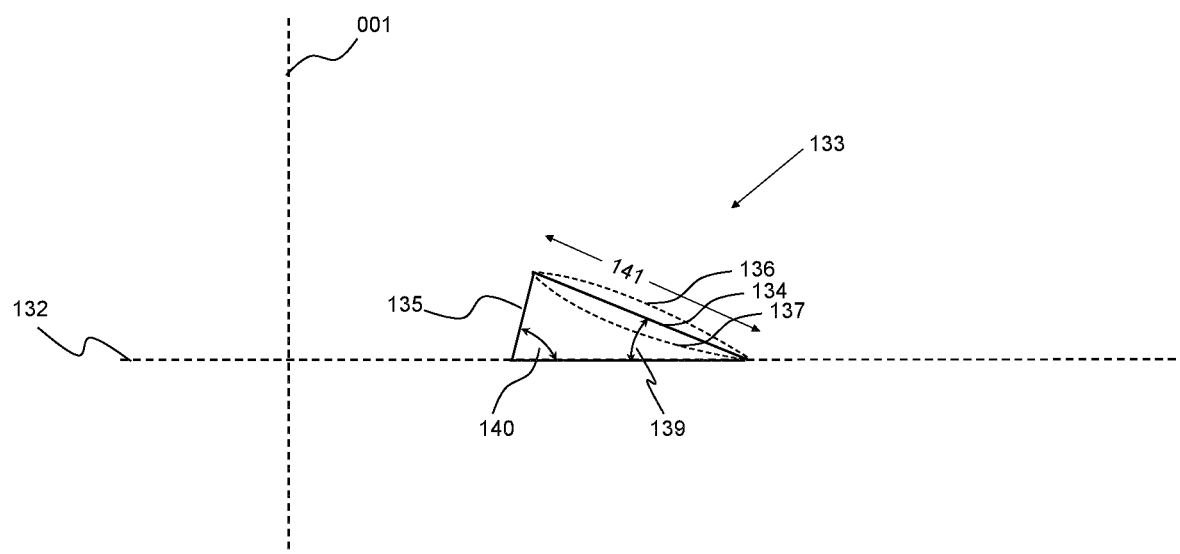
FIG. 2 shows a cross-sectional view of a section from a second reflector of the lighting device.

FIG. 2 shows a cross-sectional view of a section 133 from the plurality of sections 133 as shown in FIG. 1. Each section of the plurality of sections 133 has a first angle 139 enclosed by the first section surface 134 and the second plane 132. The first angle 139 may be greater than 0 degrees and less than or equal to 40 degrees. The first section surface 134 can be flat or curved such as a concave 137 or a convex shape 136. The first section surface 134 has a length 141 that is chosen from a range between 0.2 mm to 5 mm. Because the first section surface 134 is configured to face away from the center axis 001, the light output 111 is reflected towards the first reflector 102 as shown in FIG. 1.

In FIG. 1, a first set of sections 133 are arranged to face the left side of the first reflector 102 with respect to the center axis 001, while a second set of sections are 133 are arranged to face the right side of the first reflector 102 with respect to the center axis 001. Therefore, the first set of sections 133 are configured to reflect the light output 111 on the left side of the first reflector 102, and the second set of sections 133 are configured to reflect the light output 111 on the right side of the reflector. Therefore, the plurality of section 133 as shown in FIG. 1 can be arranged in zones such that sections can reflect light in specific directions or areas, thereby creating desired beam shape, distribution, and/or pattern. For the purpose of disinfection, this may also allow a certain level of illumination, i.e. dosage of disinfecting radiation to reach a certain area.

The sections may be arranged to be concentric on the second reflective surface, rather than discrete sections that are as a set or group facing towards a specific part of the first reflective surface. The plurality of sections may be arranged adjacent to each other, such that there is no gap between the two neighboring sections.

In FIG. 2, each section of the plurality of sections 133 has a second angle 140 enclosed by the second section surface 135 and the second plane 132, and the second angle 140 is greater than 50 degrees and less than or equal to 90 degrees. The second angle 140 may be the complement of the first angle 139. In the context of the present invention, the term 'complement' may be understood as a second angle 140 value=(90 degrees—the first angle 139 value). If the second angle 140 is a complement of the first angle 139, then the second section surface 135 may be light reflective. Such a light reflective surface may result in some retro-reflection, causing recycling and mixing of the light output at the light emission window of the light source. Otherwise, the second section surface can be absorptive for providing more control over the beam shapes, distributions, and/or patterns.

Figure 3:
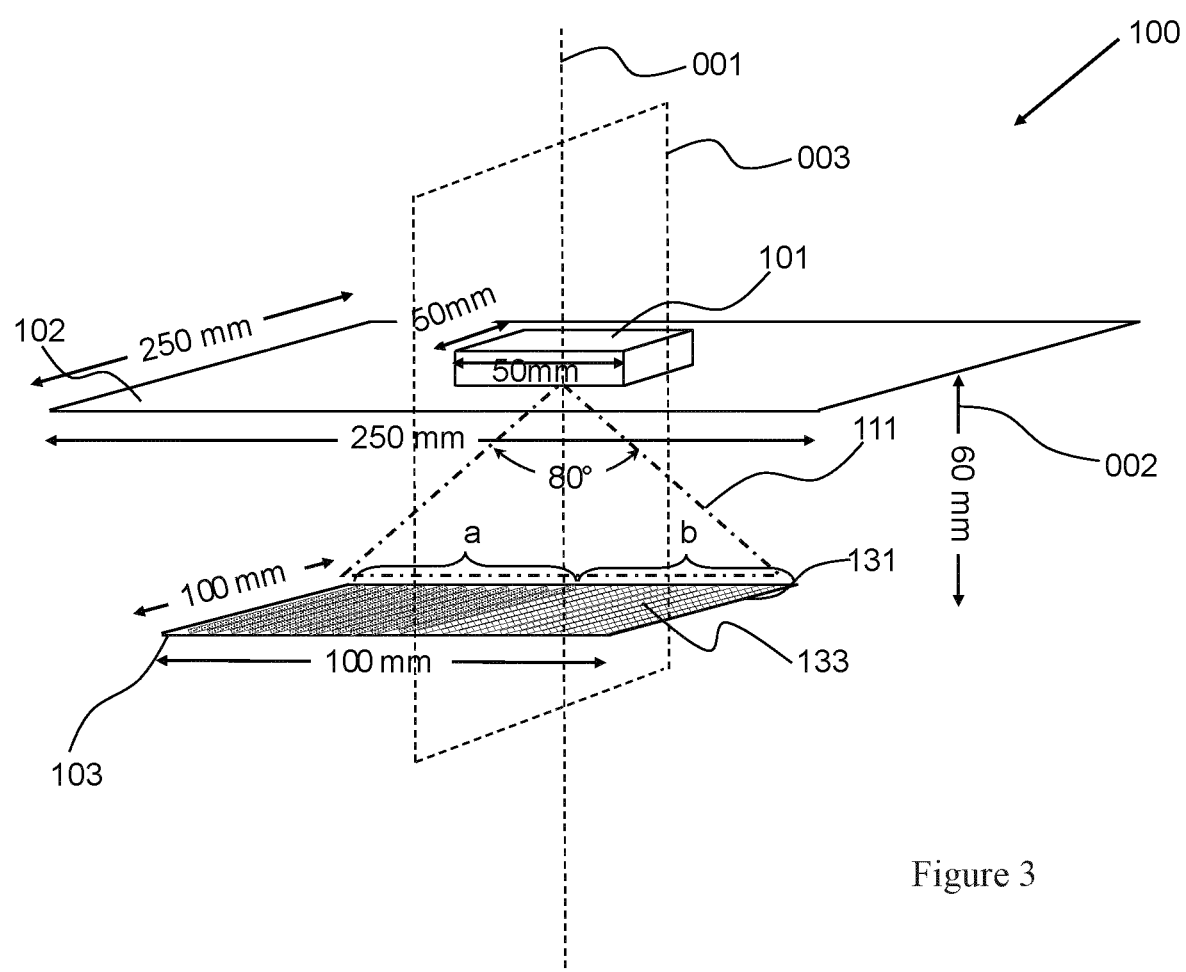
FIG. 3 shows a perspective view of a lighting device.

FIG. 3 shows a perspective view of a lighting device 100. The light source 101 has a tile shape, similar to an excimer lamp. The light source 101 has a center axis 001 and a center plane 003 passing through the center axis 001. The light source 101 has a dimension of 50 mm by 50 mm and in operation, can emit light output 111 having a full-width half-maximum of 80 degrees, i.e. the majority of the light output 111, e.g. at least 80%, is within an angle of 40 degrees or less with the center axis 001. The first reflector 102 is flat and has a square perimeter having dimensions of 250 mm by 250 mm. The second reflector 102 also is presented to be flat with a square perimeter having dimensions of 100 mm by 100 mm. The distance 002 between the first reflector 102 and the second reflector 103 is 60 mm. The light output 111 is directed towards a second reflective surface 131 of the second reflector 102. The second reflective surface 131 comprises a plurality of sections 133, as shown in FIGS. 1 and 2. A first zone, a of the plurality of sections 133 can be considered as a first set of sections, where the first section surfaces are facing the left part of the first reflector 102, with respect to the center plane 003. A second zone, b of the plurality of sections 133 can be considered as a second set of sections, where the first section surfaces are facing the right part of the first reflector 102, with respect to the center plane 003. The first section surfaces are considered to be light reflective towards the light output 111. The first reflector 102 has a first reflective surface that is facing the second reflective surface 131, as shown in FIG. 1. The first reflective surface is assumed to be specularly reflective. Although, a skilled person can also assume that the first reflective surface having a similar plurality of sections as shown in the second reflective surface. Or that the plurality of sections to be present at the first reflective surface only, while the second reflective surface is flat with specular reflection properties.

Figure 4:
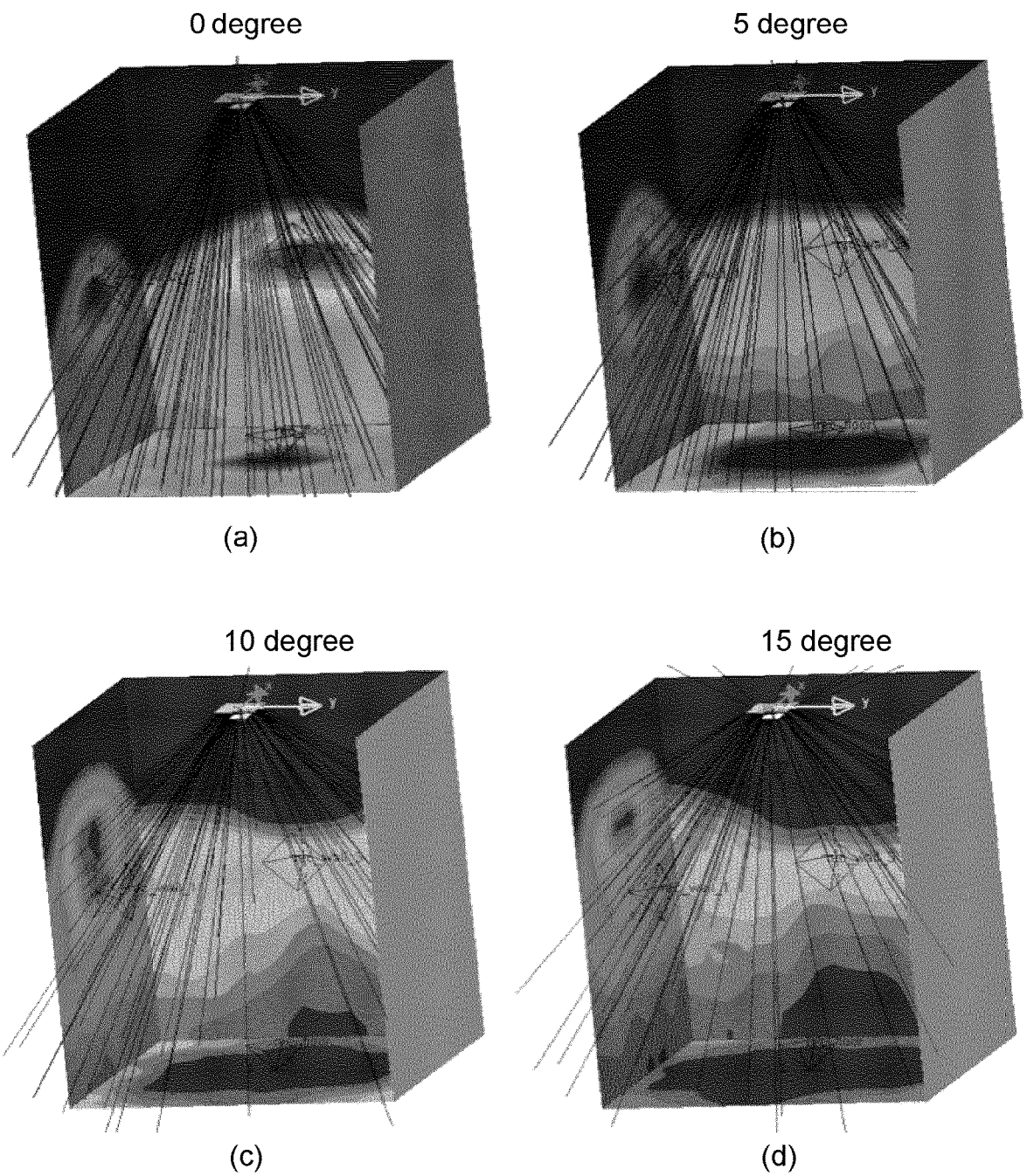
FIGS. 4(a) to (d) show simulation results for a lighting device with each section having a first angle equal to 0 degrees, 5 degrees, 10 degrees, and 15 degrees, respectively.

The above-mentioned conditions, as presented in FIG. 3 are considered for a simulation to understand the dependency of the radiation pattern or beam shape with respect to the first angle of the first section surface (the first angle of the first section surface is shown in FIG. 2). In FIG. 4, it is shown that the exact irradiation pattern on the walls and floor can be designed by changing the first angles of the first section surface. As shown in FIG. 2, the first angle 139 is defined by the enclosure between the first section surface 134 and the second plane 132. FIGS. 4(a) to (d) show simulation results for a lighting device 100 as shown in FIG. 3, with each section 133 having a first angle equal to 0 degrees, 5 degrees, 10 degrees, and 15 degrees, respectively.

In FIG. 4(a), the first angle is equal to 0 degrees, i.e. the second reflective surface is flat, having no patterns but specularly reflective, similar to the first reflective surface. In this case, the walls and parts of the floors are homogeneously illuminated. Therefore not much control over the beam shape or distribution, without changing the distance between the first reflector and the second reflector.

In FIG. 4(b), the first angle is equal to 5 degrees. Also, as shown in FIG. 3, the plurality of sections 133 are arranged in two zones, a and b. Therefore, the light reflected from the first reflective surface reaches two specific zones on two opposite walls, then their neighboring walls.

In FIGS. 4(c) and (d), the first angle is further increased to 10 and 15 degrees. As a result, the light is also reflected from the first reflective surface at higher angles and enable better control of beam shape and/or distribution and hence a more safe lighting device. Hence, the two specific zones on two opposite walls are illuminated strongly compared to their neighboring wall. In addition, high-intensity distinct spots are created at higher positions on the opposite walls when compared to the FIGS. 4(a) and (b). In view of the germicidal system, these high-intensity distinct spots may be disinfection areas where high dosage of disinfecting radiation is needed. If the closed space depicted in FIG. 4 is assumed to be an elevator space, one such high-intensity distinct spot can be the control panel in the elevator.

From FIG. 4(a) to (d), it can be understood that the orientation of the plurality of sections and the first angle of the plurality sections may allow precise control of the beam shape, distribution, and/or pattern. A further variation of the beam shape, distribution, and/or pattern can be realized by combining the plurality of sections on the first reflective surface.

The plurality of sections may be identical to each other when being arranged on the first reflective surface and/or the second reflective surface. The plurality of sections may be not identical to each other, meaning each of the plurality of sections may have different lengths or different first angles when compared to other sections from the plurality of sections. Such combinations may also allow a multitude of choices in terms of beam shapes, distributions, and/or patterns.

The lighting device 100 as shown in FIGS. 1 and 3 may be part of a luminaire. For such a luminaire, having an interchangeable second reflector and/or the first reflector may allow a user to realize different beam shapes, distribution, and/or patterns from a single luminaire.

It should be noted that the above-mentioned embodiments illustrate rather than limit the invention and that those skilled in the art will be able to design many alternative embodiments without departing from the scope of the appended claims. In the claims, any reference signs placed between parentheses shall not be construed as limiting the claim. Use of the verb "to comprise" and its conjugations does not exclude the presence of elements or steps other than those stated in a claim. The article "a" or "an" preceding an element does not exclude the presence of a plurality of such elements.

The mere fact that certain features are recited in mutually different dependent claims does not indicate that a combination of these features cannot be used to advantage. The various aspects discussed above may be combined in order to provide additional advantages. Further, the person skilled in the art will understand that two or more embodiments may be combined.

The invention claimed is:

1. A lighting device comprising:
   a light source configured to provide, in operation a light output,
   a first reflector comprising a first reflective surface, and
   a second reflector comprising a second reflective surface,
   wherein the first reflective surface is configured to face the second reflective surface,
   wherein the light source is configured to emit the light output towards the second reflective surface,
   wherein the second reflective surface comprises a plurality of sections, each section comprising a first section surface that faces away from a center axis of the light source and a second section surface that faces towards the center axis, and
   wherein the first section surface comprises a light reflective surface,
   wherein the second reflective surface comprises a plurality of sections, each section comprising a first section surface that faces away from a center axis of the light source, wherein the first section surface comprises a light reflective surface configured to reflect at least a part of the light output away from the light source, towards the first reflective surface of the first reflector;
   wherein the second reflective surface is configured in a second plane that is perpendicular to the center axis, and each section of the plurality of sections has a first angle enclosed by the first section surface and the second plane, and the first angle is greater than 10 degrees and less than or equal to 40 degrees; and
   wherein the first reflector and the second reflector are flat and are configured parallel to each other.

2. The lighting device according to claim 1, wherein the light output has a spectral power distribution in a range of 100 to 400 nm.

3. The lighting device according to claim 1, wherein the first reflective surface is at least partially configured in a first plane that is perpendicular to the center axis, and the light source has a light emission plane that is substantially parallel to the first plane.

4. The lighting device according to claim 1, wherein the first angle is greater than 10 degrees and less than or equal to 20 degrees.

5. The lighting device according to claim 1, wherein the first section surface is flat or curved.

6. The lighting device according to claim 1, wherein the first section surface has a length that is chosen from a range between 0.2 mm to 5 mm.

7. The lighting device according to claim 1, wherein the second reflective surface is configured in a second plane that is perpendicular to the center axis, and each section of the plurality of sections has a second angle enclosed by the second section surface and the second plane, and the second angle is greater than 50 degrees and less than or equal to 90 degrees.

8. The lighting device according to claim 1, wherein the second section surface comprises a light reflective, or light absorptive surface.

9. The lighting device according to claim 1, wherein the first reflective surface and the second reflective surface is separated by a distance that is chosen from a range between 20 to 150 mm.

10. The lighting device according to claim 1, wherein the first reflective surface encloses a first area and the second reflective surface encloses a second area, and a ratio of the first area and the second area is chosen from a range between 1.1 to 4.

11. The lighting device according to claim 1, wherein each section of the plurality of sections has the same first angle.

12. The lighting device according to claim 1, wherein each section of the plurality of sections has different first angles.

13. The lighting device according to claim 1, wherein each section of the plurality of sections is configured concentrically on the second reflective surface.

14. A luminaire comprising at least one lighting device according to claim 1.

15. The luminaire according to claim 14, wherein the second reflector is replaceable.

* * * * *